US 6,662,805 B2

(12) United States Patent
Frondoza et al.

(10) Patent No.: US 6,662,805 B2
(45) Date of Patent: Dec. 16, 2003

(54) METHOD FOR COMPOSITE CELL-BASED IMPLANTS

(75) Inventors: Carmelita G. Frondoza, Woodstock, MD (US); David S. Hungerford, Cockeysville, MD (US); Alan H. Shikani, Ruxton, MD (US); Abraham J. Domb, Efrat (IL); David J. Fink, Baltimore, MD (US); Leonard Bloom, Owings Mills, MD (US)

(73) Assignees: The Johns Hopkins University; Chondros, Inc.

( * ) Notice: Subject to any disclaimer, the term of this patent is extended or adjusted under 35 U.S.C. 154(b) by 211 days.

(21) Appl. No.: 09/922,909

(22) Filed: Aug. 6, 2001

(65) Prior Publication Data

US 2001/0051834 A1 Dec. 13, 2001

Related U.S. Application Data

(63) Continuation-in-part of application No. 09/825,632, filed on Apr. 4, 2001, which is a continuation-in-part of application No. 09/712,662, filed on Nov. 14, 2000, which is a continuation-in-part of application No. 09/275,319, filed on Mar. 24, 1999, now Pat. No. 6,378,527.

(51) Int. Cl.$^7$ .............................................. A61B 19/00
(52) U.S. Cl. ..................................... 128/898; 623/23.72
(58) Field of Search ......................... 623/23.72–23.75; 128/898

(56) References Cited

U.S. PATENT DOCUMENTS

| | | | |
|---|---|---|---|
| 5,041,138 A | 8/1991 | Vacanti et al. ................ 623/16 |
| 5,830,708 A | 11/1998 | Naughton ................... 435/70.1 |
| 5,855,608 A | * 1/1999 | Brekke et al. ............... 424/487 |
| 5,855,619 A | 1/1999 | Caplan et al. ................. 623/11 |
| 5,965,125 A | * 10/1999 | Mineau-Hanschke .... 424/93.21 |
| 6,027,744 A | * 2/2000 | Vacanti et al. .............. 424/426 |
| 6,197,061 B1 | 3/2001 | Masuda et al. .......... 623/11.11 |

* cited by examiner

Primary Examiner—Corrine McDermott
Assistant Examiner—Thomas Barrett
(74) Attorney, Agent, or Firm—Armstrong, Westerman & Hattori

(57) ABSTRACT

This invention is a method for the implantation of a combination of cells or cell-microcarrier aggregates wherein one component comprises a solid implantable construct and a second component comprises an injectable formulation. For example, in one embodiment, the solid implant may be first implanted to fill the majority of the cavity receiving the implant, and then cells or cell-microcarrier aggregates in an injectable format, with or without the addition of gelling materials to promote rapid gelling in situ, may be injected into spaces surrounding the solid implant in order to secure the solid implant in the site and/or to promote rapid adherence and/or integration of the solid implant to surrounding tissues. Also contemplated in this embodiment is that the cellular composition of the injectable component may differ from that of the solid component. For example, the solid implant may result from the culturing of chondrocytes on microcarriers or scaffolds, thereby resulting in an implant having cartilage-like properties, whereas the injectable cells or aggregates may result from the culturing of stem cells, resulting thereby in cells capable of producing cells of a chondrogenic, fibroblastic, myoblastic or osteoblastic phenotype. In this example, cells in the injectable aggregates may promote the fixation to or rapid integration of the solid cartilage implant into surrounding cartilage, connective tissue, muscle or bone, respectively.

9 Claims, 4 Drawing Sheets

Fig 1C

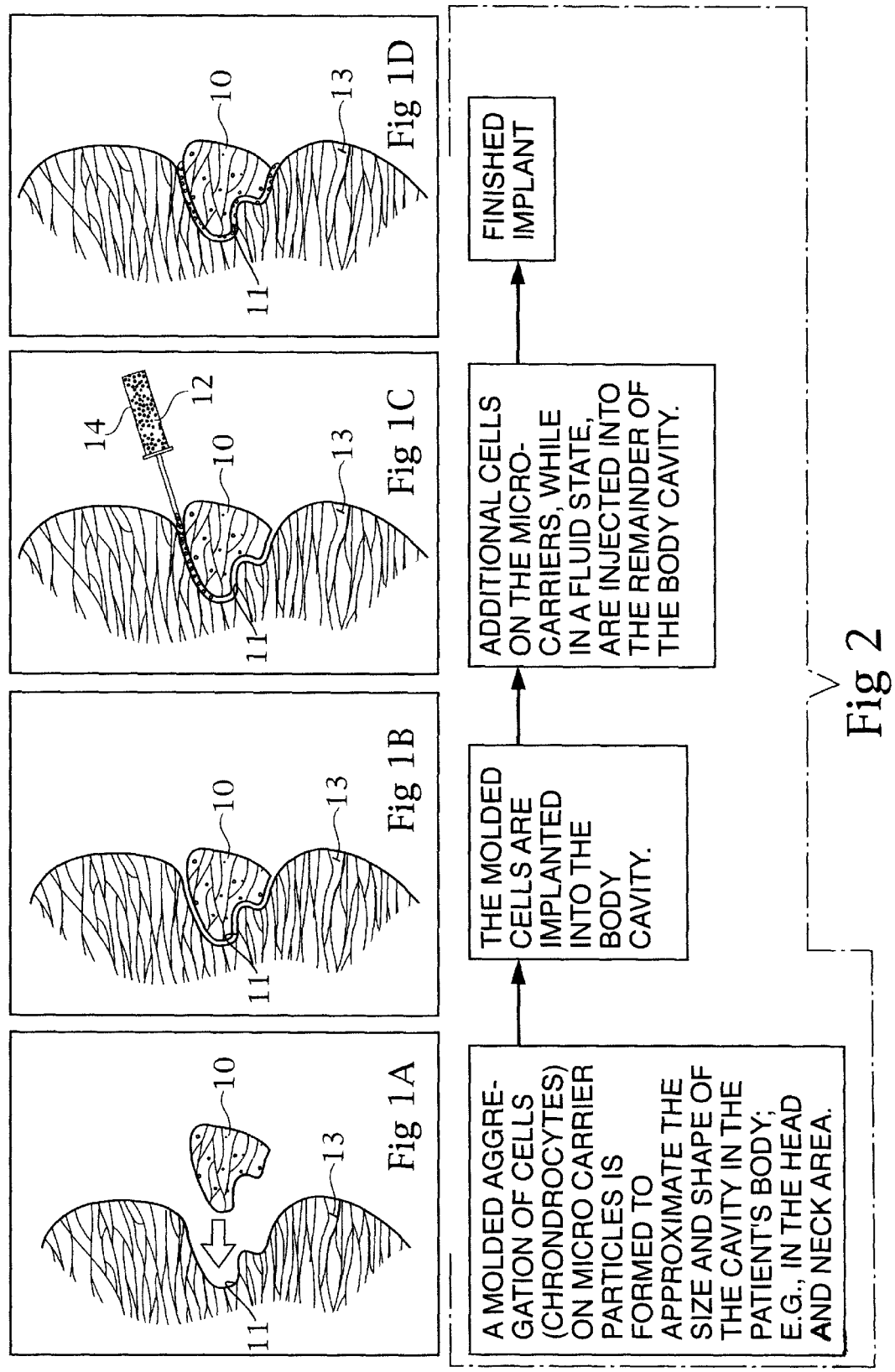

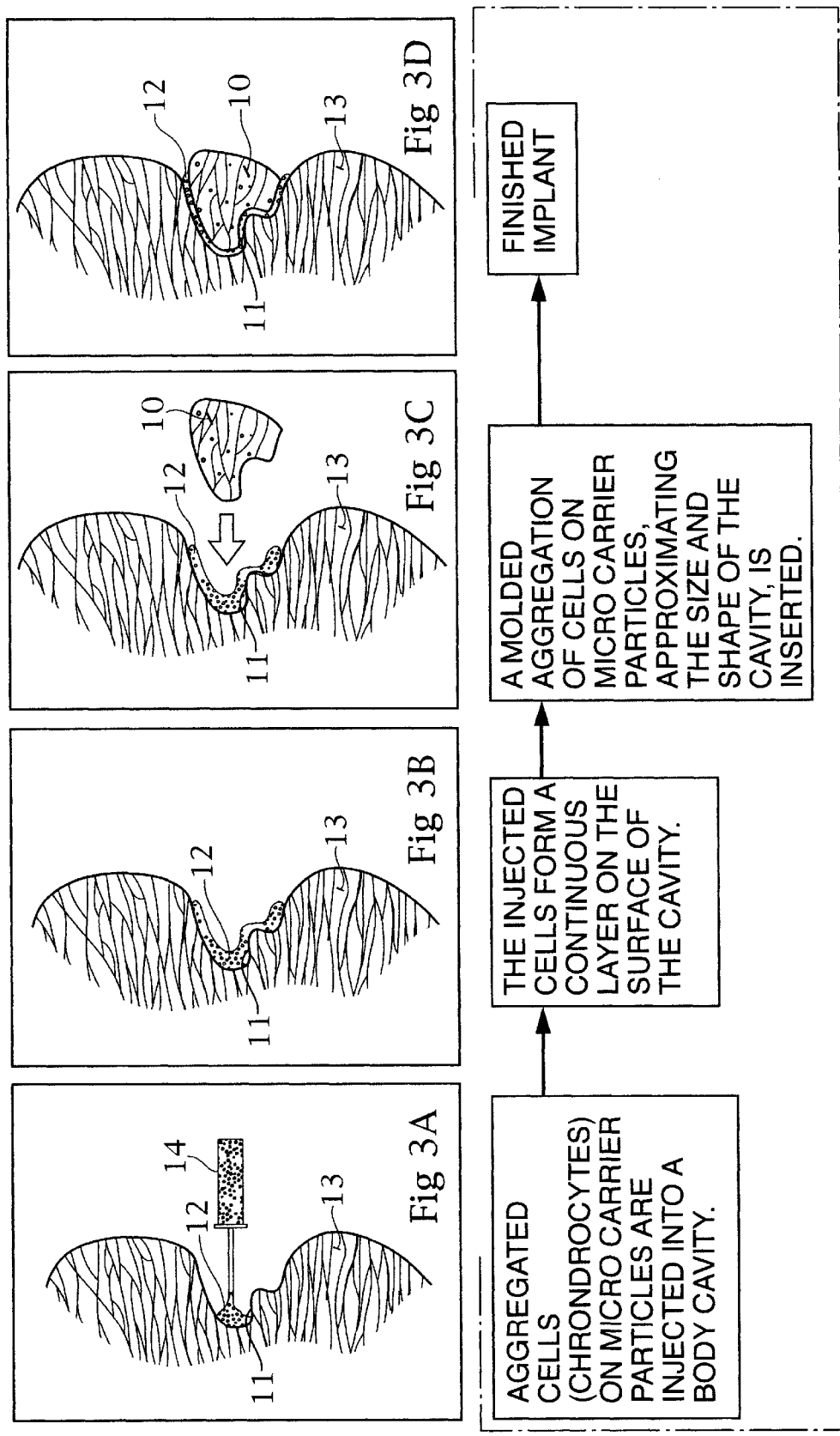

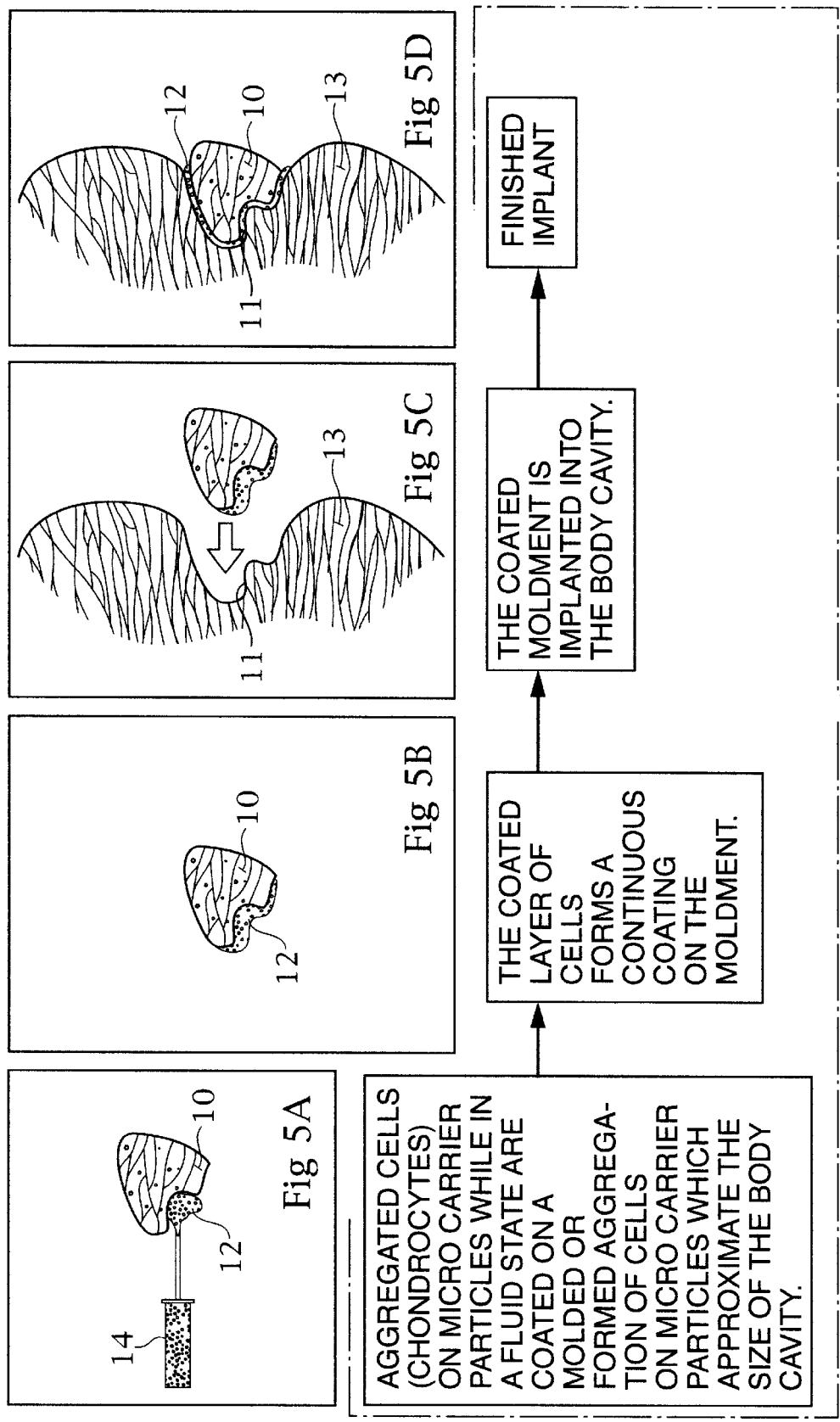

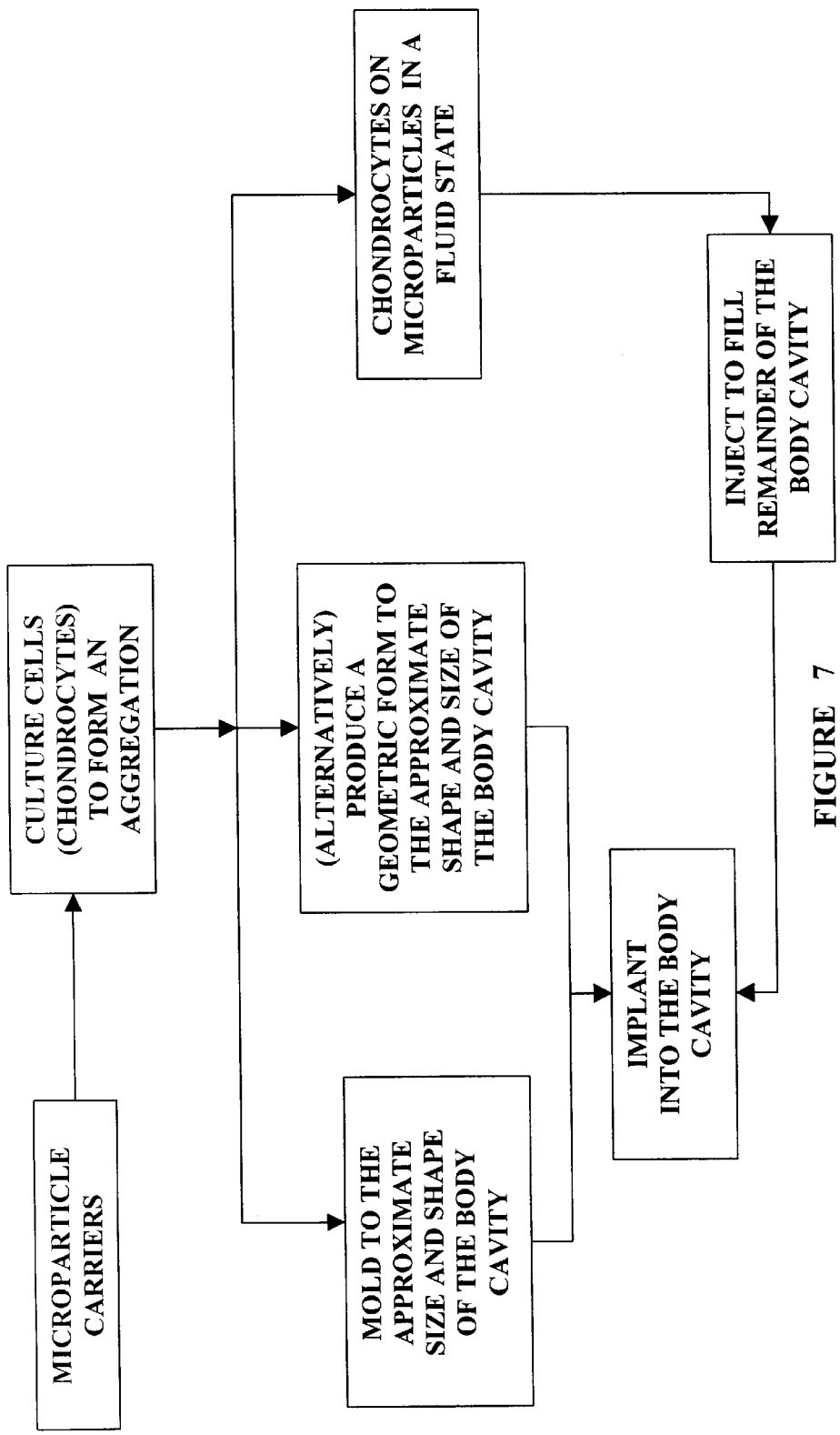

METHOD FOR COMPOSITE CELL-BASED IMPLANTS

RELATED APPLICATIONS

This application is a continuation-in-part of application Ser. No. 09/825,632 filed Apr. 4, 2001 for "Methods for Fabricating Cell-Containing Implants", which in turn is a continuation-in-part of application Ser. No. 09/712,662 filed Nov. 14, 2000, which in turn is a continuation-in-part of application Ser. No. 09/275,319 filed Mar. 24, 1999 now U.S. Pat. No. 6,378,527, the contents of which prior applications are incorporated in their entirety by reference herein.

FIELD OF THE INVENTION

The herein disclosed invention finds applicability in the field of preparation and implantation of tissue substitutes for tissue replacement and for prosthesis.

BACKGROUND OF THE INVENTION

The present inventors have previously described a microcarrier spinner culture system that facilitated maintenance of chondrocytic phenotype while enhancing proliferation. Articular chondrocytes were grown on dextran or crosslinked collagen microcarrier beads under controlled pH, oxygen levels, nutrient supply and mechanical agitation conditions. This represents a great advantage over the traditional static monolayer culture system, which facilitates proliferation but leads to a fibroblastic shift in phenotype. Likewise, it offers an alternative to the battery of three-dimensional gel or scaffold systems, which include agarose or collagen gels, calcium alginate gel, mixed fibrin-alginate gels, three-dimensional meshes of resorbable polymers such as polylactides or polyglycolides, and encapsulation in alginate beads. These latter culture techniques facilitate the maintenance of a chondrocytic phenotype, but are limited in maximizing proliferation.

A previously disclosed invention (referred to as PTO Ser. No. 09/825,632) can be described as a method of preparing cells for implantation comprising allowing cells (e.g., chondrocytes) to grow on microcarrier particles for an extended period of time and to secrete extracellular matrix components, thereby producing a cell-microcarrier aggregate useful for transplantation to a patient. The cell-microcarrier aggregates can be implanted directly or further cultured inside a mold that has been shaped to configure the geometry of the area of the body receiving the cells for transplantation. When further cultured in a mold, cell-microcarrier aggregates are consolidated into an implantable structure for repair or replacement of missing or diseased tissue. The microcarrier used to prepare the aggregate is a biocompatible, biodegradable material. This method also anticipates that cell-microcarrier aggregates, or consolidated implants prepared therefrom by further culturing in a mold, may be cryopreserved by standard methods in order to maintain cell viability and aggregate structure for future implantation or analysis.

In another embodiment of the PTO Ser. No. 09/825,632 invention, cell-microcarrier aggregates are cultured to provide a suspension of individual aggregates that may be implanted by injection by syringe or by other endoscopic or arthroscopic instruments suitable for their implantation into a diseased or damaged anatomic site. In this embodiment, cell-microcarrier aggregates may be implanted without any additional material to bind the aggregates together after implantation. Alternatively, a material capable of polymerizing or gelling after implantation may be mixed with the aggregate suspension prior to implantation in order to improve the fixation and localization of the aggregates after implantation, to stimulate more rapid consolidation of the aggregates in vivo, or to promote more rapid integration of the aggregates into the surrounding tissue.

Numerous studies of the implantation of solid tissue-engineered implants, especially soft-tissue analogs such as cartilage-like implants, have demonstrated that the fixation of these constructs to surrounding tissues is a significant problem in the long-term localization of the construct at the implantation site and to the subsequent integration of the implant with the surrounding tissue. Cartilage constructs such as those produced by culturing chondrocytes on biodegradable scaffolds, for example, have been reported by researchers at MIT and Advanced Tissue Sciences to "seal off" around their peripheral surfaces, resulting in inhibiting on blocking the integration of these surfaces with surrounding articular cartilage following implantation. In particular, partial- or full-thickness defects in articular cartilage are especially difficult to treat because mechanical fixation by sutures results in further damage to the surrounding cartilage without resulting in firm fixation of the implant. The use of tissue glues such as fibrin or cyanoacrylate formulations, may result in initial fixation of the implant, but may also inhibit or block the cellular processes leading to the bridging of the interface. The invention described herein provides a method for improving the integration of such solid constructs into the surrounding host tissue by incorporating a suspension of cells or cell-microcarrier aggregates at the interface of the implanted and surrounding host tissue, thereby stimulating the integration of the implanted and host tissues.

Prior Art Patents

Masuda (U.S. Pat. No. 6,197,061) is for a method of preparing a transplantable cartilage matrix and its method of production. Autologous chondrocyte implantation is taught. Cell culture takes place in alginate beads. Cell culture can take place over a period of 7 to 14 days or longer.

Vacanti et al (U.S. Pat. No. 6,027,744) teach methods for generating new tissue using a hydrogel and tissue precursor cells delivered to a support and allowing the gel-cell composition to solidify within the support structure.

SUMMARY OF THE INVENTION

The herein disclosed invention proposes several alternative methods for implanting tissue into a body cavity for the purpose of repairing the cavity. The methods employ in combination, for example, a solid aggregate of cells and microcarrier particles and a fluid composition of cells and microcarrier particles. In use the fluid composition serves to better fix the solid aggregate in the cavity to be repaired. These alternative methods are described in detail in the figures and description set forth herein.

Definition of abbreviations used herein:

TGF-β—Transforming Growth Factor-β

BMP—Bone Morphogenetic Protein

PDGF—Platelet Derived Growth Factor

FGF—Fibroblast Growth Factor

DESCRIPTION OF THE INVENTION

Contemplated in this invention is the implantation of a combination of (1) cell-microcarrier aggregates or cell-scaffold or cell-free biomaterial formulations in a solid implantable format; and (2) cells or cell-microcarrier aggregates in an injectable format. In this context, a "solid" implant is a non-porous material that retains its shape during handling. A solid implant may contain a high content of water if the water is substantially retained in the implant, such as in cartilage or other connective tissue, for example. A solid implant may be produced, for example, by culturing cells in a porous scaffold until the pores of the scaffold become filled with a tissue-like matrix. For example, in one embodiment, the solid implant may be first implanted to fill the majority of the cavity receiving the implant, and then a suspension of cells or of cell-microcarrier aggregates in the injectable format, with or without the addition of gelling materials to promote rapid gelling in situ, may be injected into spaces surrounding the solid implant or on the outer surface of the solid implant and surrounding tissue in order to fill the remaining space around the solid implant and/or to secure the solid implant in the site and/or to promote rapid adherence and/or integration of the solid implant and/or provide a covering for the implant to surrounding tissues. Alternatively, the injectable formulation may first be applied to the site intended to receive the implant, then the solid implant construct may be inserted into the site. In this embodiment, the injectable formulation may serve to seat the solid construct into the defect, thereby helping to fix the implant in place and to promote future integration of the implant with the surrounding tissue(s). Finally, the injectable formulation may be coated onto the solid implant prior to implantation.

Also contemplated in this invention is that the cellular composition of the injectable component may differ from that of the solid component. For example, the solid implant may result from the culturing of chondrocytes, thereby resulting in an implant having cartilage properties, whereas the injectable aggregates may result from the culturing of stem cells, resulting thereby in cells having the capability of producing cells of a fibroblastic, myoblastic or osteoblastic phenotype. In this example, cells in the injectable aggregates may promote the rapid integration of the solid cartilage implant into surrounding soft tissue, muscle or bone, respectively. Cells are typically seeded onto the microcarriers at low density ($1-4 \times 10^3$ cells per $cm^2$), and mixing the cells and microcarriers together for periods sufficient for the cells to adhere to the microcarrier beads (2–4 hours). Microcarrier particles may be in the size range of 100–500$\mu$, with the preferred size predominantly in the range of 100–400$\mu$.

The microcarrier may be inorganic or organic resorbable materials suitable for maintaining seeded cells in culture. Inorganic materials include, for example: calcium phosphates, calcium carbonates, calcium sulfates or combinations of these materials. Organic materials might include, for example: biopolymers such as collagen, gelatin, hyaluronic acid or chemically derived modifications of hyaluronic acid, chitin, chitosan or chitosan derivatives, fibrin, dextran, agarose, or calcium alginate, particles of tissue such as bone or demineralized bone, cartilage, tendon, ligament, fascia, intestinal mucosa or other connective tissues, or chemically modified derivatives of these materials. Organic materials might also include synthetic polymeric materials, including, for example: polylactic acid, polyglycolic acid or copolymers or combinations of the two, polyurethanes, polycarbonates, poly-caprolactones, hydrogels such as polyacrylates, polyvinyl alcohols, polyethylene glycols, or poly-ethyleneimines, or any other synthetic polymers that can be produced in appropriate bead form.

In the production of an injectable formulation, cells or cell-microcarrier aggregates may be implanted without any additional material to bind the aggregates together after implantation. Alternatively, a material capable of polymerizing or gelling after implantation may be mixed with the aggregate suspension prior to implantation in order to improve the fixation and localization of the aggregates after implantation, to stimulate more rapid consolidation of the aggregates in vivo, or to promote more rapid integration of the aggregates into the surrounding tissue. Examples of such binding materials are blood, bone marrow, bone marrow concentrates, fibrin glues, collagen, combinations of fibrin glues and collagen, transglutaminase-catalyzed binding systems, hyaluronic acid, calcium alginate gels, chitosan derivatives capable of gelling at body temperature, hydrogels such as polyacrylates, polyvinyl alcohols, polyethylene glycols, or polyethyleneimines, or similar materials with suitable gelling compositions. In situ gelling of these materials may be initiated by thermal, enzymatic or chemical catalysts, pH or ionic strength changes or photo-initiation procedures.

Other bioactive factors, including, but not limited to, growth factors, cytokines, antibodies, adhesion factors and intergrins, may also be incorporated into the injectable formulation to promote cell proliferation and/or differentiation, and/or improve fixation or integration of the implants into the surrounding tissue(s). Such factors may include, for example, TGF-$\beta$, BMPs, PDGF, FGFs, interleukins and the like.

Although, the herein disclosed invention has been characterized as using chondrocytes, it may be embodied using any cells that secrete extracellular matrix components suitable for causing the cells or microcarrier-cell suspension to aggregate or to adhere to surrounding tissue in suspension culture, in suitable molding devices, or in situ following injection into a body cavity or tissue. Such cells may also include, for example, osteoblasts, myoblasts, keratinocytes, fibroblasts such as those harvested from tendon, ligament, skin, meniscus or disk of the temporomandibular joint or intervertebral joint, or multi-potent stem cells that are capable of differentiating into matrix-producing cells, including mesenchymal stem cells, pluripotent stem cells from muscle, fat or skin, or embryonic stem cells.

The herein disclosed invention also contemplates the formation of implants using a combination of one or more consolidated solid implants and an injectable cell or cell-microcarrier aggregate component capable of filling voids surrounding the solid implants or covering the implant or covering the implant and surrounding tissue and thereby, for example, to secure the solid implant in the site and/or to promote rapid adherence and/or integration of the solid implant to surrounding tissues. In this embodiment, the solid implants and injectable cells or aggregates may be derived from different cells, thereby promoting rapid integration in a specific surrounding tissue such as cartilage, muscle, bone, skin, tendon or ligament.

The herein disclosed invention is related to, and can be used with, a co-pending application (owned by a common assignee) and in which at least one of the present inventors is a joint inventor. This pending application, identified by PTO Ser. No. 09/825,632, is directed to a method of replacing a tissue or body part or filling a void in head and neck area comprising the steps of obtaining a non-diseased cell sample from the respective patient's head and neck area, rapidly growing additional cells in a bioreactor and within a predetermined mold or culture chamber which is the mirror image of the patient's tissue, body part or void, such that a molded tissue or body part is produced, and surgically implanting the molded tissue or body part as a replacement in the patient's head and neck area, such that the molded tissue or body part regenerates therein and may thereby fuse with the adjacent tissues in the head and neck area of the respective patient. The method also involves obtaining cells from the nasal area which may be chondrocytes. The method can include a scaffold made from a biodegradable microcarrier material for supporting the molded tissue or body part. In a more general embodiment of the invention, cells may be obtained from any anatomic location of the patient to receive the implant or from another human donor, and the resulting material produced by the culture method may be implanted at any location requiring the implant.

Also contemplated in this invention is a kit comprising the implant material and a means for implanting the implant into the desired anatomic site. For example, the kit may comprise a fluid suspension of cell-microcarrier aggregates, as well as, a syringe, arthroscopic device or endoscopic device used for injecting the suspension into the desired anatomic site. Alternatively, the kit may comprise a molded implant formed by further culturing the cell-microcarrier aggregates to form a solid device, along with tools for further shaping the implant intraoperatively, and tools or materials for implanting the implant by open or minimally invasive surgical procedures.

Advantages of the Method

The invention comprises the use of two formulation strategies for implantation of cells or cell-microcarrier aggregates, one as an injectable dispersion of cells or aggregates and a second formulation as a solid, semi-solid molded or formed structure of consolidated aggregates prepared by further culturing of aggregates in a mold device. This method results in an implantation procedure that fills the majority of a tissue-requiring site with an approximately-shaped solid implant and permits the remainder of the tissue-requiring site to be filled with an injectable formulation of cells or cell-microcarrier aggregates that may conform to the irregular shape of the site. The invention further provides a method to improve fixation or localization of a solid implant and/or to promote its more rapid integration into surrounding tissues, wherein the second implant comprising injectable cells or aggregates may be used to form or initiate a bond between the solid implant and the surrounding tissue.

With reference to the Drawings

FIGS. 1–6 are schematic representations of applying cell aggregates to fill a body cavity.

In the block diagram of FIG. 2, corresponding to FIGS. 1A–1D, respectively, an aggregate of cells and microcarrier particles 10 are inserted into the body cavity 11, corresponding to (FIG. 1A and FIG. 1B); and additional cells on microcarrier particles in the fluid state (denoted by 12) are injected between the surface of the body cavity 11 and the cell-microcarrier particle aggregate 10 (FIG. 1C and FIG. 1D) via a syringe 14 to assure an integral fit between the cell aggregate 10 and the tissue 13. Of course, the microcarrier particles in the fluid state could be applied over the aggregate of cells and microcarrier particles.

In the block diagram of FIG. 4, FIGS. 3A–3D, respectively, cells on microcarrier particles in the fluid state 12 are first injected by the syringe 14 to coat the surface of the body cavity 11 (FIGS. 3A and 3B); and then the molded aggregate of cells on the microcarrier particles 10 are inserted (FIG. 3C) to form the finished implant (FIG. 3D).

With reference to the block diagram of FIG. 6, corresponding to FIGS. 5A–5D, respectively, cells on microcarrier particles in the fluid state 12 are coated by the syringe 14 onto a formed aggregation of cells 10 which approximate the body cavity 11 (FIGS. 5A and 5B); and then the coated formed aggregation of cells 10 is implanted into the body cavity 11 (FIGS. 5C and 5D).

With reference to FIG. 7, there is shown a flow-chart of alternative methods of implanting aggregates of cells on microcarrier particles into a body cavity.

EXAMPLES

Example 1

Formation of Solid Tissue Implants

In Example 1 of PTO Ser. No. 09/825,632, one of the present inventors demonstrated that nasal chondrocytes propagated in microcarrier spinner culture would proliferate and produce extracellular matrix components similar to that produced by articular chondrocytes. Cartilage was obtained from five patients during nasal septum reconstruction. Chondrocytes isolated by collagenase digestion were directly seeded at $4 \times 10^3$ cells/cm$^2$ onto Cellagen microcarriers (100–400 cm$^2$, derived from bovine corium, (ICN, Cleveland, Ohio)) or in monolayer culture. Monolayer and microcarrier spinner cultures were incubated at 37EC, 5% $CO_2$ for fourteen days. Chondrocytes were harvested and cell samples enumerated in trypan blue vital dye. To analyze for proteoglycan production, cells were pulsed for 60 hours with 50 iCi/ml, $^{35}SO_4$. The proteoglycans were extracted using 4M guanidinium HCl for 24 hours at 4° C. and radiolabeled incorporation was determined by liquid scintillation counting. Aliquots were electrophoresed on 0.6% agrose-1.25 polyacrylamide gels and then autoradiographed. The Dc protein assay from BioRad was used to assess protein concentration in the cell-associated fractions (CAF). The protein concentration in the CAF was used to normalize the total CPM in each fraction. Replicates of the cells were frozen for subsequent RNA isolation. Gene Markers were determined using RT-PCR.

Chondrocytes isolated from nasal cartilage proliferated in microcarrier spinner culture within two weeks producing cell-microcarrier aggregates with cartilage-like extracellular matrix. Cell numbers increased up to 17-fold. Cell-microcarrier aggregates further cultured began to further aggregate into a cartilage-like material that was produced within thirty days. Chondrocytes expressed collagen type II and aggrecan but not collagen type I. Propagation of chondrocytes from this cartilage site in spinner culture maintained the expression of collagen type II while decreasing the expression of collagen type I. The newly synthesized proteoglycans appeared to have a high molecular weight. Histology indicated a tissue morphology consistent with that of hyaline cartilage.

This example demonstrates that nasal chondrocytes multiply in Cellagen-microcarrier spinner culture. Thus, chondrocytes retrieved from a non-articulating cartilaginous site is able to maintain features of their original phenotype. After 30 days in culture, cell-microcarrier constructs had aggregated to form consolidated structures with hyaline cartilage-like properties. These aggregated materials would be suitable for implantation, or the cell-microcarrier aggregates formed after 7–14 days may be transferred to an Implant Assembly Unit to form a solid implant with a specific geometric shape. The construct formed by this process illustrates one type of solid formulation that may be implanted according to the instant invention. Alternatively, solid formulation may formed by the extended culturing of chondrocytes or stem cells, for example, on porous, biocompatible solid scaffolds suitable for implantation into the body. Such solid formulations have been described from many research groups including researchers at MIT, Advanced Tissue Sciences, Case Western Reserve University, Osiris Therapeutics and others.

Example 2

Formation of Injectable Tissue Implants

The cell seeded microcarriers described in Example 1 are maintained in spinner culture at 60 rpm, 37° C., 5% $CO_2$ for 14 to 21 days to allow visible secretion of extracellular matrix to take place in enriched medium (Dulbecco essential media containing NCTC-109, OPI (oxaloacetate, pyruvate, insulin), 1-glutamine, gentamycin, and fetal calf serum). The cell-microcarrier aggregates are subsequently centrifuged at 200 g for 15 minutes and 4° C. The supernatant fluid is removed and the aggregates are resuspended in a fluid medium, such as phosphate buffered saline solution, suitable for injection into the body. The resuspended aggregates are next transferred to a syringe or other suitable implantation device whereby the suspension is implanted directly into the anatomic site or cavity requiring the cartilage implant. Alternatively, the cell-microcarrier aggregates may be cryopreserved and thawed prior to injection.

This example illustrates one method for producing an injectable cell-microcarrier aggregate suspension suitable as the injectable formulation of the instant invention. Alternatively, appropriate cells may be grown in spinner or monolayer culture, harvested by enzymatic (collagenase) treatment and concentrated to an injectable suspension.

Example 3

Formation of Injectable Tissue Implants Containing a Gel-forming System

The cell-seeded microcarriers of Example 1 are maintained in spinner culture at 60 rpm, 37° C., 5% $CO_2$ for 14 to 21 days to allow visible secretion of extracellular matrix to take place in enriched medium (Dulbecco essential media containing NCTC-109, OPI (oxaloacetate, pyruvate, insulin), 1-glutamine, gentamycin, and fetal calf serum). The cell-microcarrier aggregates are subsequently centrifuged at 200 g for 15 minutes and 4° C. The supernatant fluid is removed and the aggregates are resuspended in a fluid medium, such as phosphate buffered saline solution, suitable for injection into the body. In this example, fibrinogen solution is added in concentration sufficient to form a gel in vivo, and thrombin is added in sufficient concentration to cause the formation of a fibrin gel in 5–10 minutes in vivo. The resuspended aggregates are next transferred to a syringe or other suitable implantation device whereby the suspension is implanted directly into the anatomic site or cavity requiring the cartilage implant. Rapid gelation of the fibrinogen/thrombin system promotes formation of a fibrin gel in situ that stabilizes the localization of the injected aggregates, yet permits continued secretion of extracellular matrix components. During the next 14–28 days, or after a suitable period depending on the site and the rate of degradation of the fibrin gel, the cells continue to secrete extracellular matrix, thereby consolidating the cell-microcarrier suspension into a solid cartilage-like mass.

This example illustrates one method for producing an injectable cell-microcarrier aggregate suspension containing a gel-forming system suitable as the injectable formulation of the instant invention. Alternatively, other compositions may be used, such collagen, combinations of fibrin/collagen, transglutaminase-catalyzed binding systems, hyaluronic acid, calcium alginate gels, chitosan derivatives capable of gelling at body temperature, hydrogels such as polyacrylates, polyvinyl alcohols, polyethylene glycols, or polyethyleneimines, or similar materials with suitable gelling compositions. In situ gelling of these materials may be initiated by thermal, enzymatic or chemical catalysts, pH or ionic strength changes or photo-initiation procedures.

Example 4

Implantation of Composite Cell-based Implants into Craniofacial Tissues

A solid implant construct comprising autologous nasal septal chondrocytes on bioresorbable polylactic acid micro carrier beads is produced by the methods described in Example 1.

An injectable implant formulation comprising nasal septal chondrocytes on bioresorbable polylactic acid microcarrier beads is produced by the methods described in Example 2.

A defect in a human nose or ear is filled by a combination of the solid implant and the injectable formulation by the following procedure:

1. The lesion is exposed and prepared for receiving the implant by cleaning, debriding and/or modifying the defect site to form a shape suitable for receiving the implant;
2. The solid implant is cut to the approximate size and shape of the lesion and then placed into the lesion site;
3. A syringe containing the injectable formulation of cells or cell-microcarrier aggregates is used to deliver the suspension into the spaces surrounding the solid implant;
4. The incision is closed by sutures.

This example illustrates a method for implanting a composite of a solid implant and an injectable formulation of cells or cell-microcarrier aggregates to reconstruct a defect in craniofacial tissue.

Example 5

Implantation of Composite Cell-based Implants in Articular Joints

A solid implant construct comprising autologous articular chondrocytes on a bioresorbable polylactic acid scaffold is produced by the methods described in Example 1.

An injectable implant formulation comprising allogeneic mesenchymal stem cells in an injectable phosphate buffered saline solution containing fibrinogen and thrombin is produced by the methods described in Example 3.

A partial thickness lesion in the articular cartilage of a knee is filled by a combination of the solid implant and the injectable formulation by the following procedure:

1. The lesion is evaluated by arthroscopic methods and prepared for receiving the implant by cleaning, debriding and/or modifying the defect site to form a shape suitable for receiving the implant;
2. A arthroscopic delivery tool containing the injectable formulation of cells is used to coat the surface of the lesion with the formulation;
3. The solid implant is cut to the approximate size and shape of the lesion, arthroscopically placed into the lesion site, observed until the fibrin glue sets;
4. The arthroscopic tools are removed and incisions closed by standard methods.

This example illustrates a method for implanting a composite of a solid implant by using an injectable formulation of cells in a fibrin glue to fix the solid implant to the lesion site and to promote rapid integration of the solid implant construct into the surrounding cartilage tissue.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. A method for replacing a tissue or body part by filling a cavity or lesion of the tissue comprising (1) preparing a solid cell-containing implant from cells; (2) preparing an injectable cell-containing formulation of cell-microcarrier aggregates; (3) coating the surface of said cavity or lesion of the tissue with the injectable cell-containing formulation; and (4) implanting the solid cell-containing implant into said cavity or lesion of the tissue such that the cavity or lesion of the tissue is in contact with the injectable cell-containing formulation.

2. The method of claim 1 wherein the cells are chondrocytes.

3. The method of claim 1 wherein the cells are selected from chondrocytes; osteoblasts; fibroblasts derived from skin, tendon, ligament, meniscus, disk or any other connective tissue; stem cells derived from bone marrow stroma, muscle, skin or other stem cell-containing tissue; embryonic stem cells; or combinations of these cells that may be seeded onto the microcarrier.

4. The method of claim 1 wherein the cells used to prepared the solid implant differ from the cells used to prepare the injectable cell-containing formulation.

5. The method of claim 1 wherein the solid cell-containing implant is prepared by culturing cells on a solid scaffold.

6. The method of claim 1 wherein the solid cell-containing implant is prepared by culturing cells on microcarrier particles.

7. The method of claim 1 wherein the injectable cell-containing formulation is prepared by culturing cells on microcarrier particles.

8. The method of claim 1 wherein the injectable cell-containing formulation comprises a suspension of cells in a medium suitable for injection.

9. The method of replacing a tissue or body part or filling a void in a patient's head or neck area comprising the steps of obtaining a non-diseased, cell sample from the respective patient's head and neck area, rapidly growing additional cells obtained from said cell sample in a bioreactor to produce a suspension of cell-microcarrier aggregates, and further culturing some of the cell-microcarrier aggregates within a predetermined mold which is the mirror image of the patient's tissue, body part or void, such that a molded tissue, body part or void is produced, and surgically implanting the molded tissue, body part or void in combination with an injectable suspension of cell-microcarrier aggregates as a replacement in the patient's head and neck area, such that the implant regenerates therein and fuses with the adjacent tissues in the head and neck area of the respective patient.

* * * * *